United States Patent
Pilkington et al.

(10) Patent No.: US 10,702,656 B2
(45) Date of Patent: Jul. 7, 2020

(54) PLUNGER LOCKING ASSEMBLY FOR A FAT TRANSFER SYRINGE

(71) Applicant: Black Tie Medical Inc., San Diego, CA (US)

(72) Inventors: Mary L. Pilkington, San Diego, CA (US); Marc Pilkington, San Diego, CA (US); Mariano C. Riego de Dios, San Diego, CA (US)

(73) Assignee: Black Tie Medical Inc., San Diego, CA (US)

( * ) Notice: Subject to any disclaimer, the term of this patent is extended or adjusted under 35 U.S.C. 154(b) by 63 days.

(21) Appl. No.: 16/000,834

(22) Filed: Jun. 5, 2018

(65) Prior Publication Data

US 2018/0280623 A1    Oct. 4, 2018

Related U.S. Application Data

(63) Continuation-in-part of application No. 15/154,890, filed on May 13, 2016, now Pat. No. 10,398,886.
(Continued)

(51) Int. Cl.
*A61M 5/315* (2006.01)
*A61B 17/00* (2006.01)

(52) U.S. Cl.
CPC .... *A61M 5/31513* (2013.01); *A61M 5/31515* (2013.01); *A61B 2017/00969* (2013.01); *A61M 2202/08* (2013.01)

(58) Field of Classification Search
CPC .......... A61M 5/31513; A61M 5/31515; A61M 2202/08; A61B 2017/00969
(Continued)

(56) References Cited

U.S. PATENT DOCUMENTS 4,906,231 A * 3/1990 Young ................. A61M 5/5013
604/110
5,651,372 A * 7/1997 Caillouette ........ A61B 10/0283
600/567
(Continued)

OTHER PUBLICATIONS

"The Tulip Instrumentation System" product sheet, 1992, The Tulip Company, San Diego, CA.
(Continued)

*Primary Examiner* — Phillip A Gray
(74) *Attorney, Agent, or Firm* — Rodney F. Brown

(57) ABSTRACT

A plunger locking assembly is provided for a syringe which has a barrel and a plunger. The barrel has a closed end with a cannula connector, an open end bounded by a peripheral lip and a barrel longitudinal axis extending between the closed end and the open end. The plunger has a plunger inner end, a plunger outer end and a plunger longitudinal axis extending between the plunger inner end and the plunger outer end. The plunger is slidably displacable within the barrel to different longitudinal lock positions and the barrel and plunger longitudinal axes are coextensive with one another. The plunger locking assembly includes a main body and a plunger locking mechanism. The main body has an inner end, an outer end and a main body longitudinal axis and is adapted to engage the plunger. The plunger locking mechanism is positioned on the main body and is adapted to lock the plunger at a fixed longitudinal lock position within the barrel to prevent further slidable displacement of the plunger into the barrel.

17 Claims, 12 Drawing Sheets

Related U.S. Application Data

(60) Provisional application No. 62/516,618, filed on Jun. 7, 2017.

(58) Field of Classification Search
USPC .......................................................... 604/222
See application file for complete search history.

(56) References Cited

U.S. PATENT DOCUMENTS

| | | | |
|---|---|---|---|
| 5,713,914 A * | 2/1998 | Lee ..................... | A61M 1/0009 604/321 |
| 6,796,969 B1 * | 9/2004 | Andersson ............ | A61M 5/322 604/110 |
| 8,469,233 B2 * | 6/2013 | Lutz ..................... | A61J 1/2096 222/1 |

OTHER PUBLICATIONS

"The Soft Touch for Soft Tissue" brochure, 1992, The Tulip Company, San Diego, CA.
"Tulip Instruments" catalog, 2010, p. 9, Tulip Products, San Diego, CA.

* cited by examiner

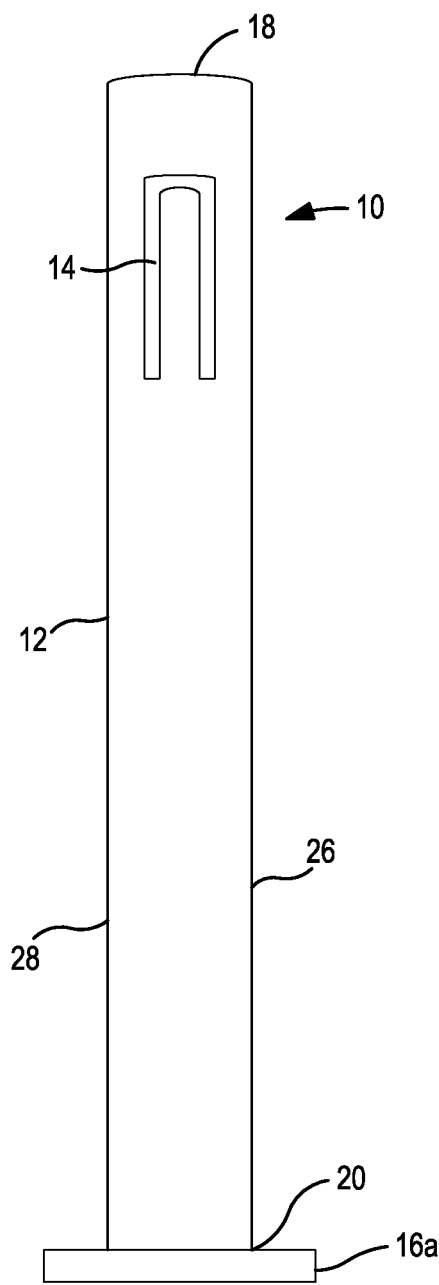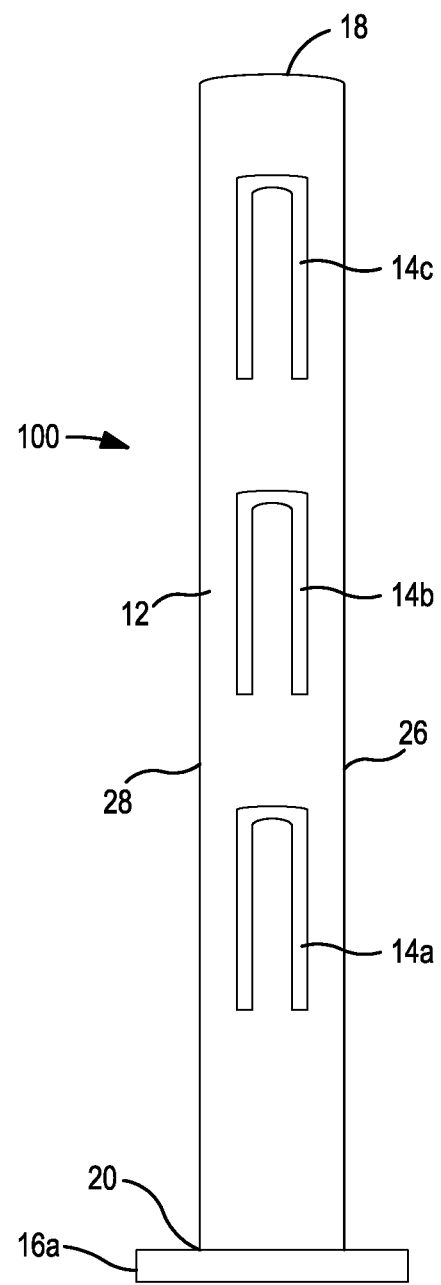
FIG. 1  FIG. 2

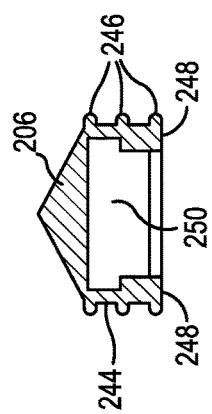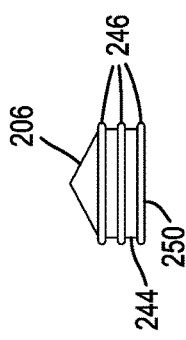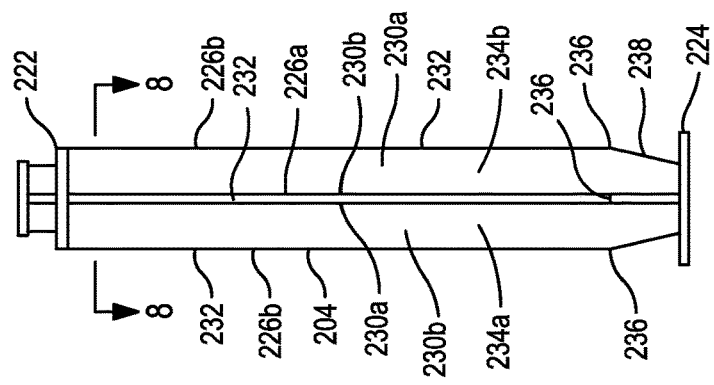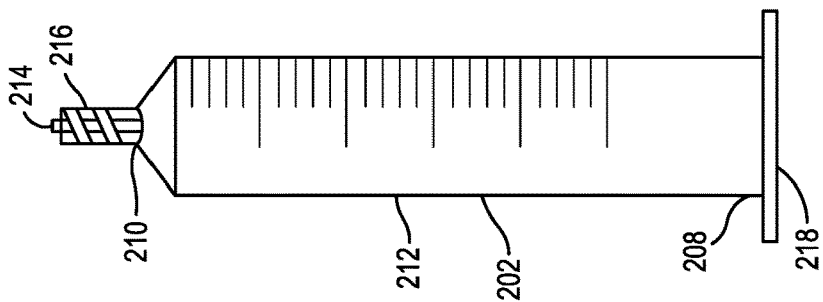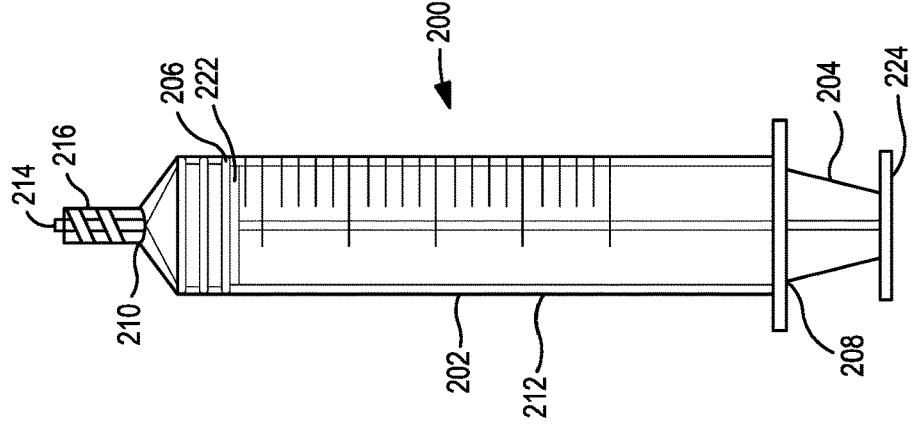

PLUNGER LOCKING ASSEMBLY FOR A FAT TRANSFER SYRINGE

This a non-provisional patent application claiming the priority of Provisional Patent Application Ser. No. 62/516,618 filed on Jun. 7, 2017.

This is also a continuation-in-part patent application of patent application Ser. No. 15/154,890 filed on May 13, 2016 which claims the priority of Provisional Patent Application Ser. Nos. 62/162,367 and 62/162,389, both filed on May 15, 2015.

Patent Application Ser. Nos. 15/154,890 and 62/516,618 are incorporated herein by reference.

BACKGROUND OF THE INVENTION

The present invention relates generally to medical devices and more particularly to devices having utility in clinical applications for fat transfer.

Fat transfer, alternately termed fat grafting, is an autologous process comprising two or more procedures or sub-processes performed in series. Fat transfer processes are typically initiated with a fat harvesting procedure, optionally followed by one or more fat conditioning procedures and concluded with a fat re-injection procedure.

Fat harvesting procedures all entail removing and recovering fat, more specifically characterized as native adipose material, from the hypodermis of a patient. The hypodermis is the subdermal or subcutaneous innermost layer of the skin which is one of the primary sites on the body where fat is produced and stored. As such, the native adipose material recovered from the hypodermis appears as an amalgam of loose connective tissue and fat lobules. On a more microscopic level, the native adipose material recovered from the hypodermis is characterized as an adipose tissue complex which is a diverse heterogeneous mixture including inter alia adipocytes, precursor adipocytes, stromal cells, stem cells, macrophages, free lipids dissociated from ruptured adipocytes, perivascular matrix, extracellular matrix and native scaffolding. Preferred harvesting sites on the body include the fatty lower layer of skin on the thighs or stomach of the patient. Fat harvesting is performed in accordance with any number of well-known techniques including liposuction or lipoplasty.

Among the optional fat conditioning procedures are centrifugation, filtration, decantation and washing of the harvested fat. Fat re-injection procedures all entail re-injecting at least a portion of the harvested fat, which has optionally been conditioned by one or more fat conditioning procedures such as those listed above, into an injection site on the body of the same patient. The injection site is different than the harvesting site, although the precise location on the body of the injection site depends on the particular clinical application for the fat transfer process. For example, potential injection sites in cosmetic applications for fat transfer include the skin of the face, breasts, cheeks, lips, buttocks, and/or chin. The re-injected fat acts as a superficial filler in cosmetic applications to desirably increase volume at the injection site and enhance the appearance of the patient. Alternate injection sites may be selected for other clinical fat transfer applications, such as for skin anti-aging, hair regeneration, restoration of sun/radiation damaged skin, restoration of abnormally scarred skin, healing of chronic flesh wounds and treatment of many musculoskeletal disorders.

A fat transfer syringe is generally the tool of choice for performing fat harvesting procedures and/or fat re-injection procedures. However, an ongoing need is recognized herein for structure that cooperatively supplements a conventional fat transfer syringe and enhances its performance and/or its ease of use as an efficient and effective fat harvesting or re-injection tool. Accordingly, it is an object of the present invention to provide structure which satisfies the above need. This object and others are accomplished in accordance with the invention described hereafter.

SUMMARY OF THE INVENTION

The present invention may be characterized as a plunger locking assembly for use in cooperation with a fat transfer syringe to perform a fat harvesting or fat re-injection procedure. The syringe has a barrel and a plunger. The barrel has a closed end with a cannula connector, an open end bounded by a peripheral lip and a barrel longitudinal axis extending between the closed end and the open end. The plunger has a plunger inner end, a plunger outer end and a plunger longitudinal axis extending between the plunger inner end and the plunger outer end. The plunger is slidably displacable within the barrel to different longitudinal lock positions and the barrel and plunger longitudinal axes are coextensive with one another.

An embodiment of the plunger locking assembly includes a main body and a plunger locking mechanism. An alternate embodiment of the plunger locking assembly includes the main body, the plunger locking mechanism and a plunger retention member. Yet another alternate embodiment of the plunger locking assembly includes the main body, the plunger locking mechanism and a means for retaining the main body in engagement with the plunger.

In any case, the main body has an inner end, an outer end and a main body longitudinal axis and is adapted to engage the plunger. The plunger locking mechanism is positioned on the main body and is adapted to lock the plunger at a fixed longitudinal lock position within the barrel to prevent further slidable displacement of the plunger into the barrel. The plunger retention member is adapted to retain the main body in engagement with the plunger. A preferred plunger locking mechanism includes a catch having a free end and an attached end. The attached end is attached to the main body and the free end is rotatably displaceable relative to the main body about the attached end. In accordance with one alternative the attached end is preferably attached to the main body by a living hinge. In accordance with another alternative the attached end is preferably attached to the main body by a spring.

The free end of the catch preferably has a barrel end engagement face adapted to selectively engage the lip at the open end of the barrel. The catch preferably has an unstressed position, a stressed position and a catch extension distance. The catch extension distance is at a maximum value when the catch is in the unstressed position, thereby adapting the barrel end engagement face to engage the lip at the open end of the barrel and block further slidable displacement of the plunger locking assembly and the plunger into the barrel. The catch extension distance is at a reduced value less than the maximum value when the catch is in the stressed position, thereby adapting the barrel end engagement face to clear the lip at the open end of the barrel and allow further slidable displacement of the plunger locking assembly and the plunger into the barrel.

The catch is preferably adapted to selectively transition between the unstressed position and the stressed position by rotating the free end about the attached end in response to the absence or presence of a catch depression force. When the attached end of the catch is attached to the main body by a spring, the spring is preferably adapted to automatically elastically return the catch to the unstressed position from the stressed position when the catch depression force is absent.

A preferred plunger retention member includes a first retention arm and a second retention arm both positioned at the outer end of the main body and both adapted to releasably attach to the plunger outer end. An alternative preferred plunger retention member includes a slot positioned at the outer end of the main body and adapted to receive and releasably attach to the plunger outer end.

A preferred plunger locking mechanism of the plunger locking assembly is a first plunger locking mechanism and the plunger locking assembly preferably has a plurality of plunger locking mechanisms including the first plunger locking mechanism. Each of the plurality of plunger locking mechanisms is serially positioned on the main body, each of the plurality of plunger locking mechanisms is adapted to lock the plunger at different fixed longitudinal lock positions within the barrel to prevent further slidable displacement of the plunger into the barrel, and the fixed longitudinal lock position of the first plunger locking mechanism is a first fixed longitudinal lock position.

The invention will be further understood from the drawings and the following detailed description.

BRIEF DESCRIPTION OF THE SEVERAL VIEWS OF THE DRAWINGS

The below-listed drawing figures illustrate one or more embodiments of the present invention by way of example and not by way of limitation. Common reference characters may be used among the different drawing figures to indicate the same or similar structural elements.

FIG. 1 is a front elevation view of an embodiment of a plunger locking assembly.

FIG. 2 is a front elevation view of an alternate embodiment of a plunger locking assembly.

FIG. 3 is an exemplary conventional syringe.

FIG. 4 is the barrel of the syringe of FIG. 3.

FIG. 5 is the plunger of the syringe of FIG. 3.

FIG. 6 is the stopper of the syringe of FIG. 3.

FIG. 7 is a cross section of the stopper of FIG. 6.

DETAILED DESCRIPTION OF THE INVENTION

Figure 12:
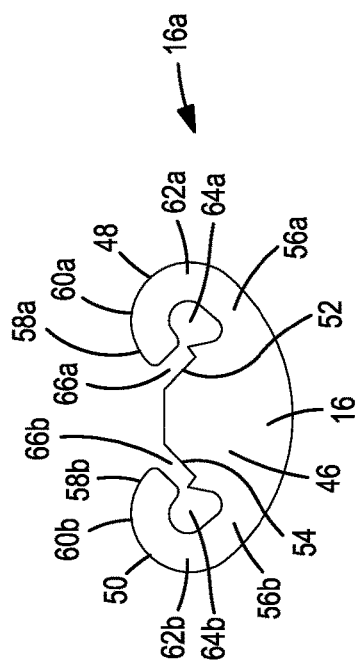
FIG. 12 is a plan view of the outer end of the plunger locking assembly of FIG. 1.
Figure 13:
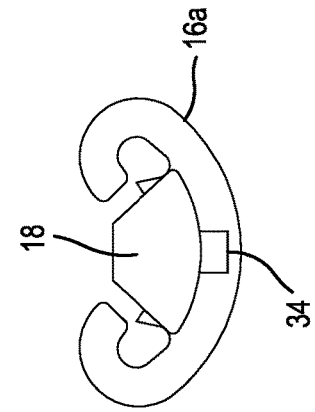
FIG. 13 is a plan view of the inner end of the plunger locking assembly of FIG. 1.

FIG. 1 shows a first embodiment of a plunger locking assembly generally designated 10 and FIG. 2 shows a second embodiment generally designated 100. Each of these embodiments 10, 100 has alternate utility in the performance of a fat harvesting procedure and/or a fat re-injection procedure when employed in cooperation with a fat transfer syringe. A syringe of the type having cooperative utility with the plunger locking assembly 10 or 100 for fat harvesting and/or re-injection procedures is an off-the-shelf medical syringe manufactured by Becton, Dickinson and Company (BD). Exemplary BD syringes are shown and described in published material on the BD website www.bd.com under the subject heading "Products/Injection," which was retrieved from the web page http://www.bd.com/us/products/category.asp on May 31, 2017. A print-out of this web page is incorporated herein by reference.

FIGS. 3-8 show a representative fat transfer syringe generally designated 200 with which the plunger locking assembly 10 or 100 can be cooperatively employed to perform a fat harvesting procedure and/or a fat re-injection procedure. The fat transfer syringe 200 is preferably an off-the-shelf, sterile, disposable, single-use syringe that includes a barrel 202, a plunger 204 and a stopper 206. The barrel 202 has an elongate hollowed out cylinder configuration with a first end 208 termed an open end, an opposite second end 210 termed a closed end, a continuous tubular side wall 212 extending between the two ends 208, 210 and a barrel longitudinal axis extending between the two ends 208, 210. The closed end 210 and side wall 212 partially enclose the interior of the barrel which is an open void space. The closed end 210 and side wall 212 are preferably integrally formed in their entirety from a disposable transparent or translucent rigid plastic. The open end 208 is substantially open across the entire diameter of the barrel 202 and is bounded by an outside edge that defines a peripheral lip extending around the circumference of the open end 208.

The closed end 210 is substantially closed across the entire diameter of the barrel 202 with the exception of a relatively small opening 214 in the closed end 210 provided by a cannula connector 216 integrally formed with the closed end 210. The opening 214 is a narrow tubular passageway extending through the cannula connector 216 that enables fluid communication between the interior of the barrel 202 and the environment external to the syringe 200. The cannula connector 216 is preferably a Luer coupler which is a conventional connector fitting known for a multitude of medical applications. A Luer coupler has either a male configuration or female configuration that couples with a Luer coupler of the opposite configuration. A finger hold 218 is integrally formed with the peripheral lip at the outside edge of the open end 208 of the barrel 202 and extends outwardly therefrom. The finger hold 218 facilitates gripping the barrel 202 during use of the syringe 200 in a manner described hereafter.

The volume of the open void space within the barrel 202 determines the volumetric capacity of the syringe 200 and, more particularly, the volumetric capacity of the barrel 202. Off-the-shelf syringes having utility herein typically have a barrel with one of several predetermined standard volumetric capacities. For example, off-the-shelf syringes are typically available having barrels with a standard volumetric capacity of 20 cc or 60 cc.

The plunger 204 has an elongate shape with a main body 220, a first end 222 termed an inner end, an opposite second end 224 termed an outer end and a plunger longitudinal axis extending between the two ends 222, 224. The main body 220 and inner and outer ends 222, 224 are all preferably integrally formed from a disposable rigid plastic so that the plunger 204 in its entirety has an integral unitary structure. The main body 220 is configured as two identically-dimensioned elongate rectangles intersecting one another at right angles along their respective longitudinal axes. This configuration gives the main body 220 the appearance of four identically-dimensioned rectangular vanes 226a, 226b, 226c, 226d, each radially emanating at right angles to one another from a common axis of intersection, which corresponds to the plunger longitudinal axis and, more particularly, the plunger central longitudinal axis 228. The reference character 226 is also sometimes used in this description with reference to any one of vanes 226a, 226b, 226c, 226d or any two or more of the vanes 226a, 226b, 226c, 226d collectively as will be apparent from the context.

Each vane 226 has first and second longitudinally-extending lateral faces 230a, 230b, respectively, on each of its planar sides. These lateral faces 230a, 230b are each longitudinally bounded by a distal edge 232 and a proximal edge. The terms proximal and distal are used in the present context in relation to the plunger central longitudinal axis 228. It is apparent that the proximal edge of the lateral faces 230a, 230b is one and the same as the common axis of intersection of the vanes 226a, 226b, 226c, 226d and is also one and the same as the plunger central longitudinal axis 228. The distal edge 232 is positioned a radial distance outward from the proximal edge 228.

The cross section of the main body 220 resembles an "X" with each branch of the "X" representing a vane 226 that divides the cross section into four quadrants. Each of the four quadrants defines a wedge-shaped longitudinal compartment 234a, 234b, 234c, 234d running along the length of the main body 220 that is bounded on two sides by opposing lateral faces 230 of serially adjacent perpendicularly-oriented vanes 226, but is otherwise open, e.g., compartment 234a is bounded by the lateral face 230a of vane 226a and the lateral face 230b of vane 226b, compartment 234b is bounded by the lateral face 230a of vane 226b and the lateral face 230b of vane 226c, etc. The reference character 234 is also sometimes used in this description with reference to any one of compartments 234a, 234b, 234c, 234d or any two or more of the compartments 234a, 234b, 234c, 234d collectively as will be apparent from the context.

A convex arc (shown by a phantom dashed line) may be drawn between the distal edges 232 of adjacent perpendicularly-oriented vanes 226 that has a curvature essentially corresponding to the concave curvature of the inside face of the side wall 212 of the barrel 202. Although the distal edges 232 of the vanes 226 are generally follow a straight line path, the path of the distal edges 232 is slightly redirected at a point proximal to the outer end 224 termed a redirection point 236. As such, the distal edges 232 angle slightly toward the plunger central longitudinal axis 228 beginning at the redirection point 236 and continuing along this angular path to the intersection of the distal edges with the outer end 224. As a result, the vanes 232 exhibit a slight inward taper as they approach the outer end 224 of the plunger 204, thereby defining a tapered (i.e., narrowing) portion 238 of the main body 220 of the plunger 204 proximal to the outer end 224.

The inner end 222 of the plunger 204 and the stopper 206 are cooperatively configured so that the stopper 206 fits over the inner end 222 and attaches thereto. As such, the inner end 222 has a disc shape with a flat surface that is oriented substantially perpendicular to the plunger central longitudinal axis 228. The stopper 206 is a unitary hollow structure having a cylindrical shape that is preferably formed from a compressible elastic material such as rubber, synthetic rubber or other like elastomeric material. The stopper 206 preferably has an open end 240, a closed end 242, an outer side wall 244 extending perpendicularly between the open and closed ends 240, 242 and a plurality of spaced-apart circumferential ribs 246 extending outwardly from the outer side wall 244. The open end 240 of the stopper 206 has a retention lip 248 extending around its inner circumferential edge. The closed end 242, outer side wall 244 and retention lip 248 in combination define an interior cavity 250 of the stopper 20, termed a retention chamber. The cylindrically shaped stopper 206 is removably mounted on the disc-shaped inner end 222 of the plunger 204 by positioning the open end 240 of the stopper 206 over the inner end 222 and press fitting the inner end 222 past the retention lip 248 into the retention chamber 250. As such, the retention lip 248 retains the inner end 222 of the plunger 204 in the retention chamber 250 of the stopper 206 so that the stopper 206 substantially encloses the inner end 222 of the plunger 204.

The diameter of the outer side wall 244 of the stopper 206, the diameter of the main body 220 of the plunger 204 (i.e., 2×vane width) and the diameter of the disc-shaped inner end 222 of the plunger 204 are each preferably about equal to the inside diameter of the barrel 202. In the present case "about equal to" means that the diameters of the outer side wall 244, main body 220 and inner end 222 are each slightly smaller than the diameter of the interior of the barrel 202. In contrast, the outside diameters of the compressible ribs 246 of the stopper 206 are each preferably slightly greater than the diameter of the interior of the barrel 202 when the ribs 246 are uncompressed. Accordingly, the plunger 204 and stopper 206 nest snugly within the interior of the barrel 202, but are still slidably displacable therein when a manual pushing or pulling force is applied to the plunger 204. The slightly oversize fit of the compressible ribs 246 in the interior of the barrel 202 provides a fluid-tight seal between the outside edge of the stopper 206 and the side wall 212 of the barrel 202. When the plunger 204 and stopper 206 are nested within the interior of the barrel 202, the barrel and plunger longitudinal axes are coextensive with one another.

The plunger 204 and stopper 206 in combination preferably have a length greater than the length of the interior of the barrel 202 so that the outer end 224 and tapered portion of the plunger 204 extend out of the open end 210 of the barrel 202 when the plunger 204 is fully depressed into the interior of the barrel 202 with the stopper 206 adjacent to the closed end 210 of the barrel 202. When the plunger 204 is nested in the barrel 202, the barrel and plunger longitudinal axes are coextensive with one another.

The outer end 224 of the plunger 204 has substantially the same configuration as the inner end 222. As such, the outer end 224 likewise has a disc shape with a flat surface that is oriented substantially perpendicular to the plunger central longitudinal axis 228. The disc-shaped outer end 224 functions as a finger pull that facilitates gripping the plunger 204 during use of the syringe 200. In particular, manually pulling on the outer end 224 displaces the plunger 204 and associated stopper 206 in a direction away from the closed end 210 of the barrel 202. Manually pushing on the outer end 224 displaces the plunger 204 and associated stopper 206 in an opposite direction toward the closed end 210 of the barrel 202.

Details of the plunger locking assembly 10 are described hereafter with reference to FIGS. 1 and 9-16. The plunger locking assembly 10 and plunger 204 are cooperatively configured so that the plunger locking assembly 10 engages and securably attaches to the plunger 204. In particular, the plunger locking assembly 10 preferably nests within one of the wedge-shaped longitudinal compartments 234 of the plunger 204 and preferably attaches to the two serially adjacent vanes 226 bounding the selected compartment 234. The plunger locking assembly 10 comprises a main body 12, a plunger locking mechanism 14 and a plunger retention member 16a. The main body 12, plunger locking mechanism 14 and plunger retention member 16a are all preferably integrally constructed together as a unitary structure from a disposable semi-rigid plastic or like material that has a degree of elasticity as a function of its thickness.

Figure 16:
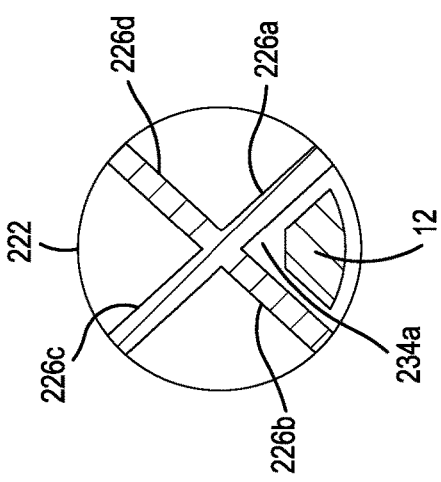
FIG. 16 is a cross section of the plunger and plunger locking assembly of FIG. 14 taken along line 16-16.
Figure 8:
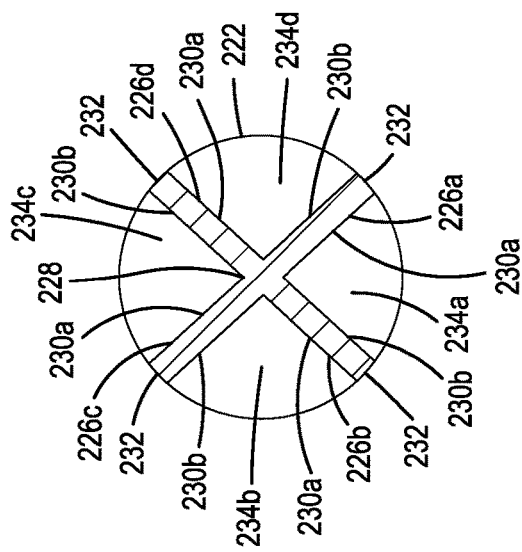
FIG. 8 is a cross section of the plunger of FIG. 5 taken along line 8-8.
Figure 15:
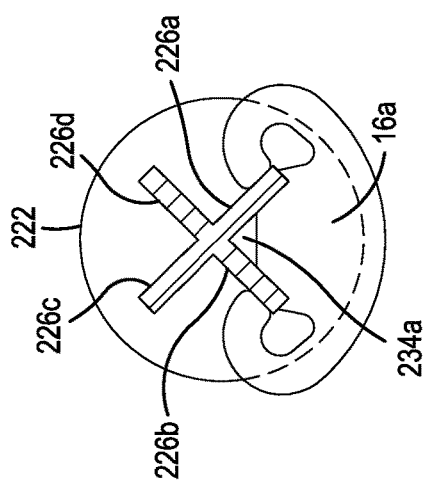
FIG. 15 is a cross section of the plunger and plunger locking assembly of FIG. 14 taken along line 15-15.
Figure 9:
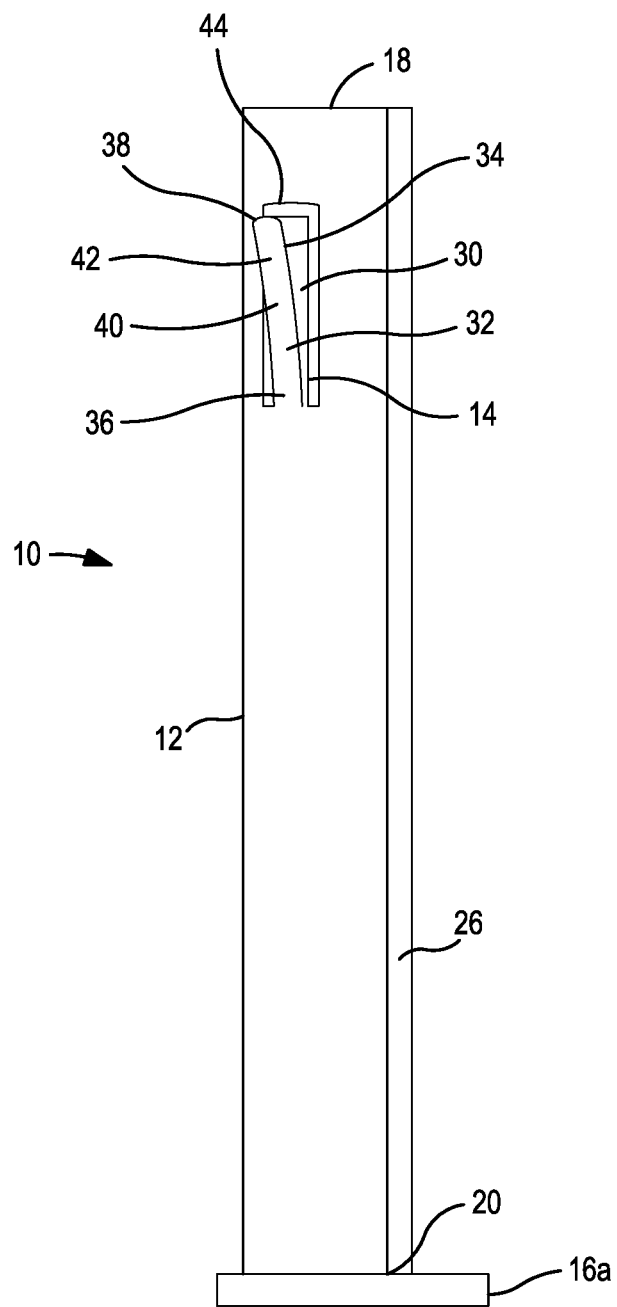
FIG. 9 is an elevation view of the plunger locking assembly of FIG. 1, but rotated about 45 degrees from the front view of FIG. 1.
Figure 11:
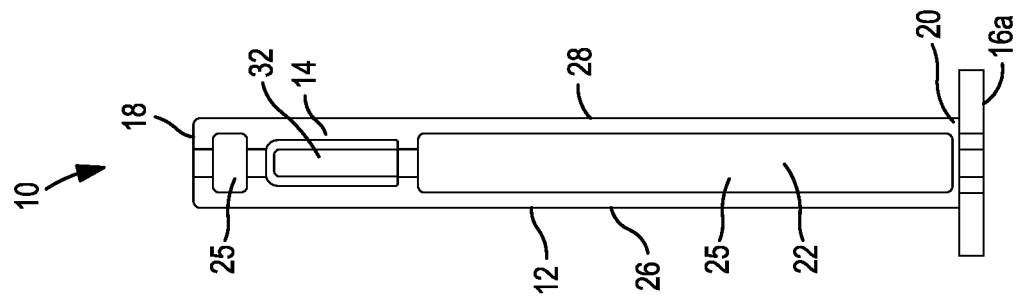
FIG. 11 is a rear elevation view of the plunger locking assembly of FIG. 1.
Figure 10:
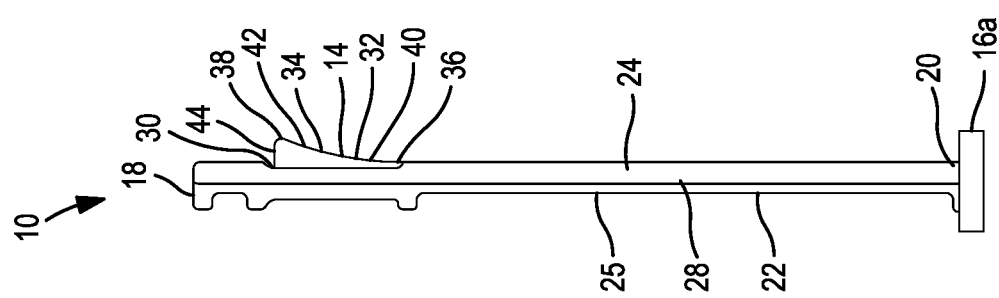
FIG. 10 is a side elevation view of the plunger locking assembly of FIG. 1.
Figure 19:
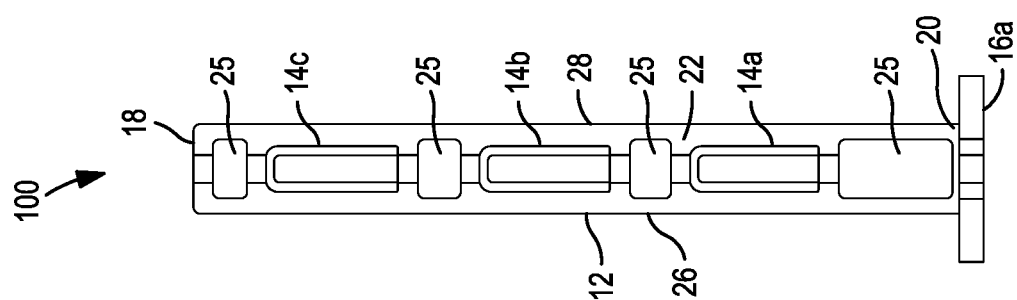
FIG. 19 is a rear elevation view of the plunger locking assembly of FIG. 2.
Figure 18:
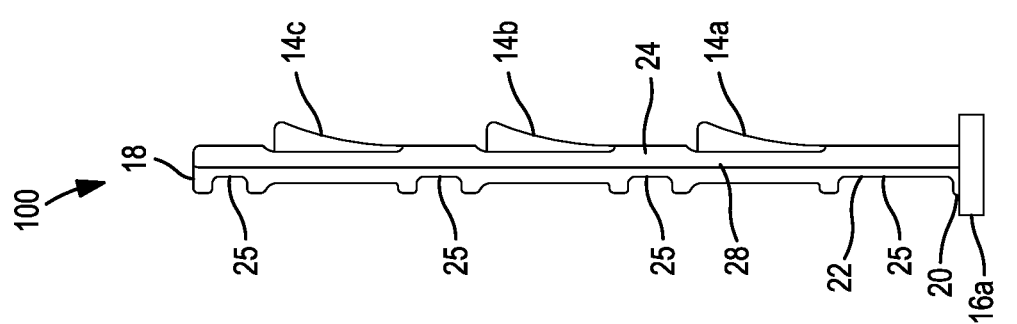
FIG. 18 is a side elevation view of the plunger locking assembly of FIG. 2.
Figure 14:
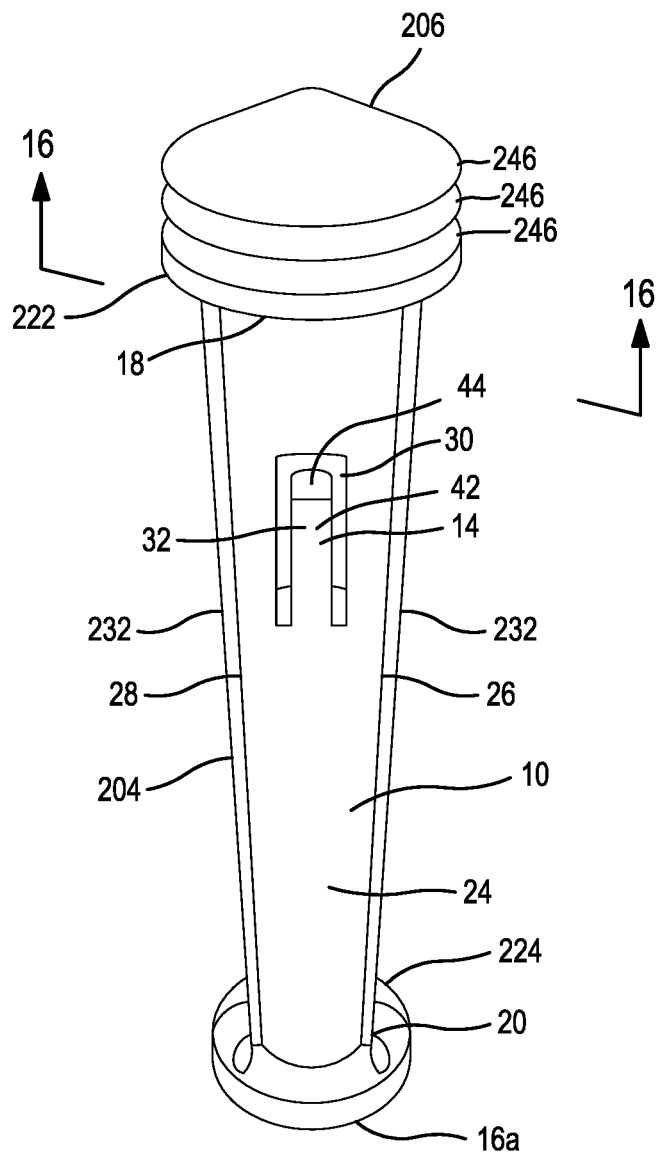
FIG. 14 is a perspective view of the plunger locking assembly of FIG. 1 mounted on the plunger of FIG. 5.
Figure 17:
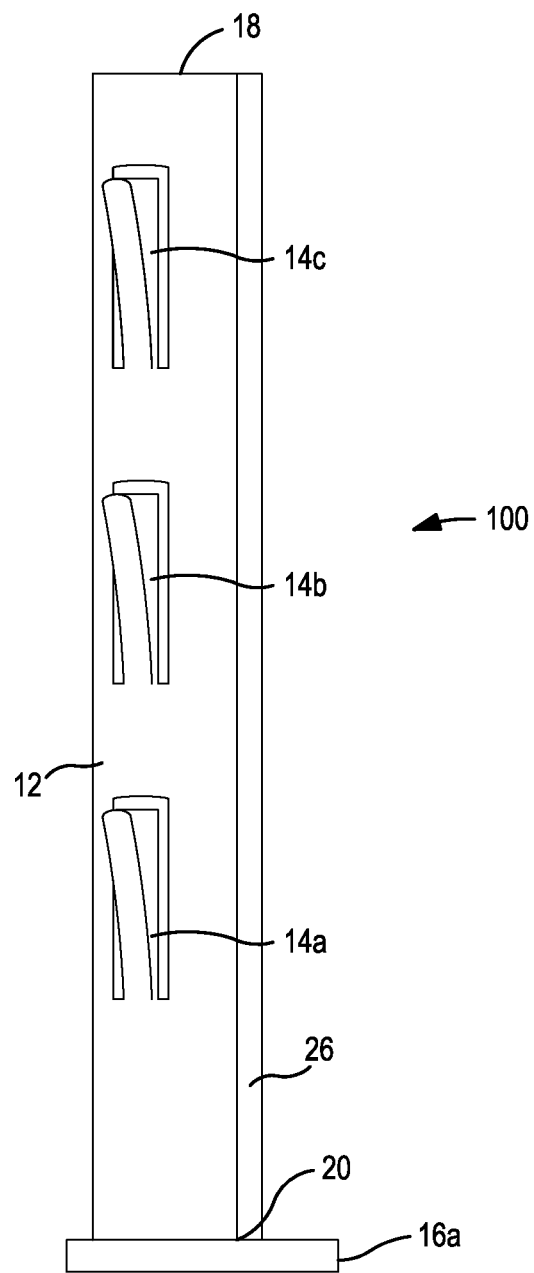
FIG. 17 is an elevation view of the plunger locking assembly of FIG. 2, but rotated about 45 degrees from the front view of FIG. 2.
Figure 20:
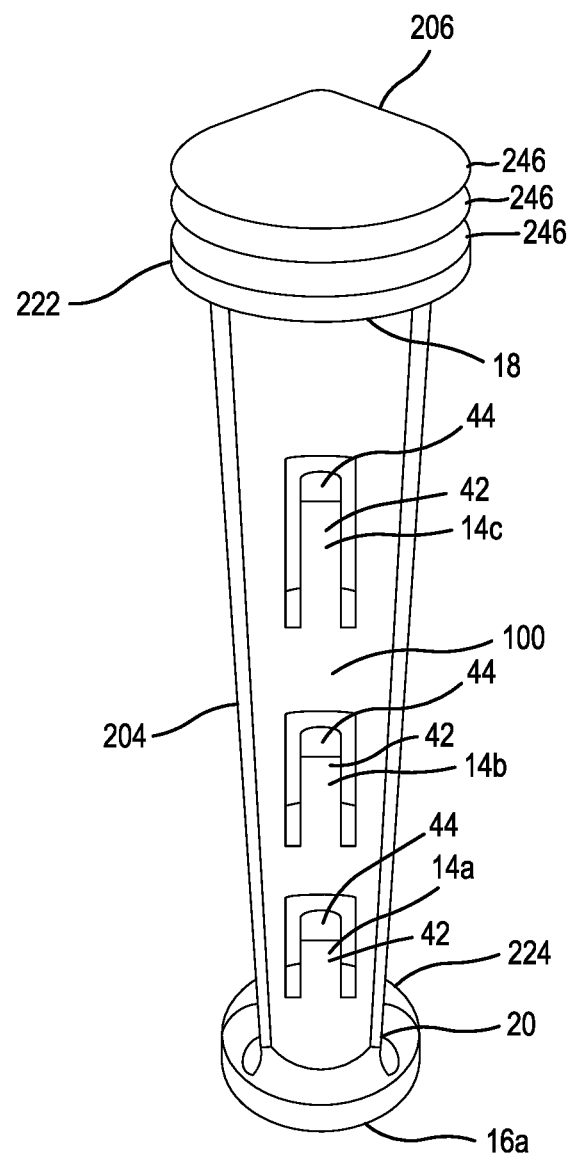
FIG. 20 is a perspective view of the plunger locking assembly of FIG. 2 mounted on the plunger of FIG. 5.

The main body 12 is an elongate structure with a wedge-like shape at least somewhat corresponding to the shape of the longitudinal compartments 234. The main body 12 has a first end 18 termed an inner end and an opposite second end 20 termed an outer end. The main body 12 also has a first face 22 termed a proximal face and an opposite second face 24 termed a distal face, both of which longitudinally extend the length of the main body 12. The terms proximal and distal are used in the present context in relation to the plunger central longitudinal axis 228 when the plunger locking assembly 10 is operably attached to the plunger 204 as shown in FIGS. 14-16 and described hereafter. The proximal face 22 has optional rectangular cut-outs 25 in the material of the proximal face 22 to reduce the weight of the main body 12 without substantially diminishing the strength and performance of the plunger locking assembly 10. It is alternatively within the scope of the present invention to omit the cut-outs 25 from the proximal face 22 so that it has an essentially smooth continuous surface. The distal face 24 is an essentially smooth continuous surface having a convex arcuate contour with a curvature that essentially corresponds to the concave curvature of the inside face of the side wall 212 of the barrel 202 and has an arc length that is essentially equal to the length of the arc drawn between the distal edges 232 of adjacent perpendicularly-oriented vanes 226 of the plunger 204.

The main body 12 additionally has a third face 26 termed a first lateral face and an opposite fourth face 28 termed a second lateral face, both of which likewise longitudinally extend the length of the main body 12. The first and second lateral faces 26, 28 are each oriented at an essentially identical acute angle relative to the distal face 24 such that the first and second lateral faces 26, 28 provide the configuration of the main body 12 with its wedge-like taper as the main body 12 extends radially inward from the distal face 24 to the proximal face 22.

The plunger locking mechanism 14 is integrally formed at a position on the main body 12 between the inner end 18 and the outer end 20 thereof, but substantially closer (i.e., more proximal) to the outer end 20 than it is to the inner end 18. The plunger locking mechanism 14 has a travel slot 30 and a locking member 32 with a catch 34 and a hinge 36. The catch 34 has a free end 38 and an attached end 40. The free end 38 is more proximal to the inner end 18 of the main body 12, i.e., is more distal from the outer end 20 of the main body 12, and the attached end 40 is more distal from the inner end 18 of the main body 12, i.e., is more proximal to the outer end 20 of the main body 12. The attached end 40 is permanently attached to the hinge 36 by virtue of their integral construction.

The hinge 36 is preferably a living hinge formed by reducing the thickness of the material of construction at the desired position of the hinge 36. The catch 34 has a profile when viewed from the side that resembles a right triangle. As such, the catch 34 has a first engagement face 42 termed a barrel interior engagement face whose side profile corresponds to the hypotenuse of the right triangle and a second engagement face 44 termed a barrel end engagement face whose side profile corresponds to a leg of the right triangle. The intersection of the barrel interior engagement face 42 and barrel end engagement face 44 at the free end 38 is an intersection line segment that extends essentially perpendicular to the plunger longitudinal axis. The distance that the intersection line segment extends beyond the distal face 24 of the main body 12 is termed a catch extension distance.

The travel slot 30 is a cut-out in the distal face 24 of the main body 12. The travel slot 30 has a substantially rectangular outer perimeter that is slightly larger than the outer perimeter of the locking member 32. The travel slot 30 is sized to enable inward (i.e., proximal) displacable rotation of the free end 38 of the catch 34 about the hinge 36 at least partially, if not completely, into the travel slot 30 during operation of the plunger locking mechanism 14, thereby varying the catch extension distance in a manner described below. In order to inwardly rotationally displace the free end 38 into the travel slot 30 and reduce the catch extension distance, an inward rotational force termed a catch depression force must be applied to the catch 34 at or proximal to its free end 38 which is sufficient to overcome the elastic resistance of hinge 36 to inward rotational displacement.

When no catch depression force is applied to the catch 34, the catch 34 is in an original unstressed position within the travel slot 30 and the catch expansion distance is at a maximum value. When the catch depression force is being applied to the catch 34, the catch 34 is in a stressed position within the travel slot 30 and the catch expansion distance is at a reduced value that is less than the maximum value. Withdrawing the catch depression force from the catch 34 when the catch 34 is in its stressed position enables the hinge 36 to function as a torsion spring and automatically elastically return the catch 34 to its original unstressed position. Thus, the catch 34 is selectively positionable in the stressed or unstressed position depending on whether a catch depression force is being applied to it or not.

The plunger retention member 16a is positioned on the outer end 20 of the main body 12 and is preferably integrally formed therewith. The plunger retention member 16a has a planar configuration that is oriented substantially perpendicular to the longitudinal axis of the main body 12. The plunger retention member 16a includes a central attachment segment 46, a first retention arm 48 and a second retention arm 50. The central attachment segment 46 is the portion of the plunger retention member 16a that is permanently attached to the outer end 20 of the main body 12 by virtue of their integral construction. The central attachment segment 46 has a substantially wedge-like configuration corresponding to the wedge-like configuration of the main body 12. As such, the central attachment segment 46 has a first lateral face 52 and an opposite second lateral face 54 which extend continuously from the first and second lateral faces 26, 28, respectively, of the main body 12. Each of the retention arms 48, 50 has a substantially identical configuration and function. In particular, each retention arm 48, 50 has an attached end 56a, 56b, a free end 58a, 58b and an extension segment 60a, 60b, respectively, that extends continuously between the attached end 56a, 56b and free end 58a, 58b.

The attached end 56a of the first retention arm 48 is permanently attached to the first lateral face 52 of the central attachment segment 46 by virtue of their integral construction such that the attached end 56a and first lateral face 52 are essentially indistinguishable from one another at their line of intersection, both being part of the same continuous structure. The extension segment 60a of the first retention arm 48 extends in a first direction away from the attached end 56a, but within the same perpendicular plane of the plunger retention member 16a, until the extension segment 60a reaches an outer reversal point 62a. When the extension segment 60a reaches the outer reversal point 62a, it curls back in a second direction opposite the first direction toward the first lateral face 52. The extension segment 60a creates and encircles a void space when it curls back on itself which is termed an expansion slot 64a. The extension segment 60a terminates at its free end 58a, which is proximal to, but separated from, the first lateral face 52 by a short distance that defines a retention slit 66a. The expansion slot 64a enables the attached end 56a of the first retention arm 48 to function as a living hinge that permits the free end 58a of the first retention arm 48 to elastically rotate a limited degree about the attached end 56a. The retention slit 66a enables the free end 58a of the first retention arm 48 to receive the distal edge 232 of a vane 226 of the plunger 204 therein and elastically retain the lateral face 230 of that vane 226 therein when the plunger locking assembly 10 is cooperatively coupled with the plunger 204 in a manner described in more detail hereafter.

As noted above, each of the retention arms 48, 50 has a substantially identical configuration and function. Accordingly, the attached end 56b of the second retention arm 50 is permanently attached to the second lateral face 54 of the central attachment segment 46. The extension segment 60b of the second retention arm 50 extends in a first direction away from the attached end 56b, but in a substantially opposite direction relative to the extension direction of the first retention arm 48, until the extension segment 60b reaches an outer reversal point 62b where it curls back in a second direction opposite the first direction of the extension segment 60b toward the second lateral face 54. It is noted that the distance between the outer reversal points 62a and 62b defines the width of the plunger retention member 16a. The curled extension segment 60b creates and encircles an expansion slot 64b. The extension segment 60b terminates at its free end 58b which is separated from the second lateral face 54 by a short distance that defines a retention slit 66b. The expansion slot 64b enables the attached end 56b of the extension segment 60b to function as a living hinge that permits the free end 58b of the second retention arm 50 to elastically rotate a limited degree about the attached end 56b. The retention slit 66b enables the free end 58b second retention arm 50 to receive the distal edge 232 of a different vane 226 of the plunger 204 therein and elastically retain the lateral face 230 of that vane 226 therein when the plunger locking assembly 10 is cooperatively coupled with the plunger 204.

The plunger locking assembly 100 is described hereafter with reference to FIGS. 2 and 17-20. The plunger locking assembly 100 is essentially identical to the plunger locking assembly 10 described above except for the number of plunger locking mechanisms they contain. In particular, the plunger locking assembly 100 has three separate plunger locking mechanisms 14a, 14b, 14c while the plunger locking assembly 10, as described above, only has one plunger locking mechanism 14. The plunger locking mechanisms 14a, 14b, 14c of the plunger locking assembly 100 are integrally formed at three different longitudinally spaced apart positions on the main body 12 between the inner end 18 and the outer end 20 thereof. Each plunger locking mechanism 14a, 14b, 14c of the plunger locking assembly 100 is essentially identical to the plunger locking mechanism 14 of the plunger locking assembly 10 described above. Additional elements that are common to both the plunger locking assembly 100 and plunger locking assembly 10 are identified by the same reference numbers in FIGS. 2 and 17-20 and the description of these elements above with respect to the plunger locking assembly 10 applies equally to the instant plunger locking assembly 100.

Additional alternate embodiments of plunger locking assemblies described hereafter are also within the scope of the present invention. In accordance with the instant alternate embodiment of the plunger locking assembly (not shown), the plunger retention member is omitted altogether from the second or outer end of the main body. As such, the main body and plunger locking mechanism(s) make up the entirety of the plunger locking assembly and are essentially structurally and functionally identical to the correspondingly named elements of the plunger locking assembly 10, 100. Therefore, the length of the instant main body from its first or inner end to its second or outer end is approximately identical to the length of the main body 12 of plunger locking assembly 10, 100 as well as to the height of the compartment 234a of the plunger 204 shown in FIG. 3 so that the instant main body fits snugly therein and is preferably retained therein by compression of its first and second ends against the disc-shaped inner and outer ends 222, 224, respectively, of the plunger 204 likewise shown in FIG. 3. It is apparent from the above that the upward and downward facing profiles of the inner and outer ends, respectively, of the instant main body closely resemble the cross-sectional profile of the main body 12 shown in FIG. 16.

Figure 27:
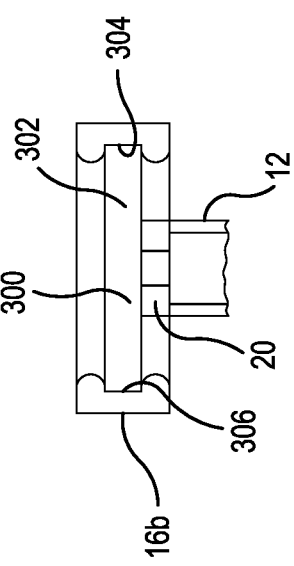
FIG. 27 is a side elevation view of an alternate embodiment of a plunger retention member.
Figure 28:
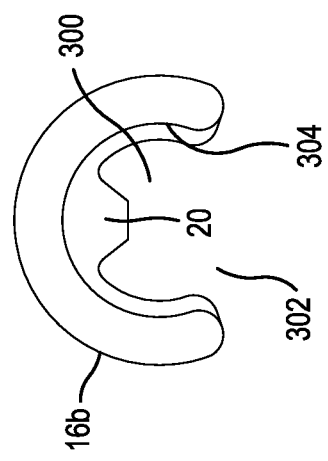
FIG. 28 is a plan view of the outer end of the plunger retention member of FIG. 27.

Another alternate embodiment of the plunger locking assembly is described hereafter with reference to FIGS. 27 and 28. The only difference between the instant plunger locking assembly and the plunger locking assembly 10, 100 is the configuration of the plunger retention member. The instant plunger retention member is referenced 16b and is positioned at the second or outer end of the main body in substantially the same manner as the plunger retention member 16a of the plunger locking assembly 10, 100. The main body and plunger locking mechanism(s) of the instant alternate plunger locking assembly are essentially structurally and functionally identical to the correspondingly named elements of the plunger locking assembly 10, 100. Accordingly, these elements are omitted from FIGS. 27 and 28 with the exception of a short segment of the main body and its outer end which are likewise referenced 12 and 20, respectively, therein.

The plunger retention member 16b is an arcuate wall having a partial tubular configuration which extends around about 0.6 of the entire circumference of the disc-shaped outer end 224 of the plunger 204 shown in FIGS. 3 and 5. As a result, the plunger retention member 16b is approximately horseshoe shaped and is semi-rigid. The plunger retention member 16b has an interior that is an open void space 300 accessible from the outside through an opening 302 left by an omitted segment in the circumferential wall that is the plunger retention member 16b. The width of the opening 302 is slightly less than the diameter of the outer end 224 of the plunger 204 so that it may be press fitted through the opening 302 into the interior void space 300. The plunger retention member 16b has an inside face 304 with a circumferential slot 306 formed therein which is continuous along the extent of the inside face 304. The height of the circumferential slot 306 is about equal to the thickness of the outer end 224 of the plunger 204 and the diameter of the circumferential slot 306 is about equal to the diameter of the outer end 224 so that the circumferential edge of the outer end 224 of the plunger 204 fits snugly within the circumferential slot 306. In sum, the void space 300, opening 302 and circumferential slot 306 are sized and configured to receive and releasably retain the outer end 224 of the plunger 204 therein. As such, the compression force of the plunger retention member 16b against the outer end 224 of the plunger 204 retains the instant plunger locking assembly in engagement with the plunger 204 when it is mounted thereon.

Figure 29:
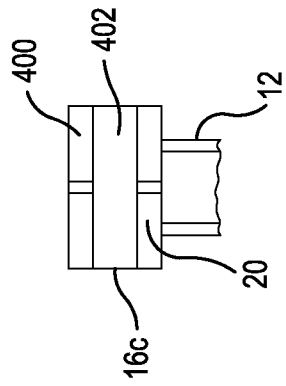
FIG. 29 is a side elevation view of an alternate embodiment of a plunger retention member.
Figure 30:
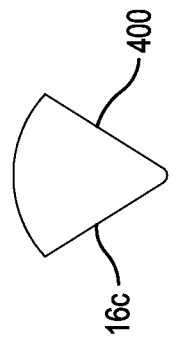
FIG. 30 is a plan view of the outer end of the plunger retention member of FIG. 29.

Yet another alternate embodiment of the plunger locking assembly is described hereafter with reference to FIGS. 29 and 30. As in the case of the immediately preceding embodiment, the only difference between the instant plunger locking assembly and the plunger locking assembly 10, 100 is the configuration of the plunger retention member. The instant plunger retention member is referenced 16c and is likewise positioned at the second or outer end of the main body in substantially the same manner as the plunger retention member 16a of the plunger locking assembly 10, 100. The main body and plunger locking mechanism(s) of the instant alternate plunger locking assembly are essentially structurally and functionally identical to the correspondingly named elements of the plunger locking assembly 10, 100. Accordingly, these elements are omitted from FIGS. 29 and 30 with the exception of a short segment of the main body and its outer end which are likewise referenced 12 and 20, respectively, therein.

The plunger retention member 16c has the wedge-shaped configuration of a quarter-section of a disc. The radius of the plunger retention member 16c is greater than the outer end 224 of the plunger 204. The plunger retention member 16c has v-shaped inside face 400 with a slot 402 formed therein. The height of the slot 402 is about equal to the thickness of the outer end 224 of the plunger 204 so that the circumferential edge of the outer end 224 of the plunger 204 fits snugly within the slot 402. As such, the compression force of the plunger retention member 16c against the outer end 224 of the plunger 204 retains the instant plunger locking assembly in engagement with the plunger 204 when it is mounted thereon.

METHODS OF USE

A method of use for the plunger locking assembly 100 in association with the fat transfer syringe 200 is described hereafter with continuing reference to FIGS. 2 and 17-20 and additional reference to FIGS. 21-24. The method is initiated by fully withdrawing the syringe plunger 204 in its entirety from the syringe barrel 202 and operatively mounting the plunger locking assembly 100 on the plunger 204 by means of a procedure termed compression mounting. Compression mounting is effected by aligning the main body 12 of the plunger locking assembly 100 with any one of the compartments 234 (e.g., 234a) formed in the main body 220 of the plunger 204 so that the first lateral face 26 of the main body 12 aligns with the lateral face 230a of a vane 226 (e.g., vane 226a) and the second lateral face 28 of the main body 12 aligns with the opposing lateral face 230b of the next serially adjacent vane 226 (e.g., vane 226b). The plunger retention member 16a of the plunger locking assembly 100 is simultaneously aligned with the tapered portion 238 of the plunger 204 corresponding to the selected compartment 234 (e.g., 234a). As such, the plunger retention member 16a is positioned immediately adjacent to the disc-shaped outer end 224 of the plunger 204, the free end 58a of the first retention arm 48 is aligned with the distal edge 232 of a vane 226 (e.g., vane 226a) and the free end 58b of the second retention arm 50 is aligned with the distal edge 232 of the next serially adjacent vane 226 (e.g., vane 226b).

Once the plunger locking assembly 100 is properly aligned with the plunger 204, the practitioner manually engages the central attachment segment 46 of the plunger locking assembly 100 and forces it radially inward toward the plunger central longitudinal axis 228. This causes the free ends 58a, 58b of the first and second retention arms 48, 50, respectively, to engage the distal edges 232 of the adjacent vanes 226 on either side of the selected compartment 234 which in turn causes the extension segments 60a, 60b to flex where they intersect the attached ends 56a, 56b of the first and second retention arms 48, 50 in the manner of a living hinge. Flexion of the extension segments 60a, 60b causes the free ends 58a, 58b of the retention arms 48, 50 to elastically rotate slightly outward about the living hinges.

As the practitioner continues to manually force the central attachment segment 46 of the plunger locking assembly 100 radially inward toward the plunger central longitudinal axis 228, the distance between the free ends 58a, 58b of the retention arms 48, 50 increases slightly from an unstressed distance to a stressed distance that is greater than the unstressed distance, thereby expanding the width of the retention slits 66a, 66b of the first and second retention arms 48, 50 and aligning the widened retention slits 66a, 66b with the distal edges 232 of the serially adjacent vanes 226 (e.g., vane 226a and vane 226b), respectively. Continued application of the radially inward directed manual force to the central attachment segment 46 of the plunger locking assembly 100 urges the distal edges 232 all into the retention slits 66a, 66b of the first and second retention arms 48, 50, respectively, which has the effect of relaxing the living hinges of the extension segments 60a, 60b and enables the free ends 58a, 58b of the retention arms 48, 50 to rotate radially inward back to their original unstressed distance apart from one another. This causes the free ends 58a, 58b of the retention arms 48, 50 to essentially "grip" the opposing lateral faces 230a, 230b of the serially adjacent vanes 226 that abut the free ends 58a, 58b.

With the plunger retention member 16a in place in abutment with the outer end 224 of the plunger 204, the practitioner urges the main body 12 of the plunger locking assembly 100 into the selected compartment 234 by applying a gentle radially inward displacement force to the distal face 24 of the main body 12, thereby completing the compression mounting procedure. Upon completion of compression mounting, the first and second lateral faces 26, 28 of the main body 12 engage the opposing lateral faces 230a, 230b of the serially adjacent vanes 226 and the inner end 18 of the main body 12 is positioned adjacent to the inner end 222 of the plunger 204. The arcuate distal face 24 of the main body 12 is essentially flush with the arc drawn between the distal edges 232 of the serially adjacent vanes 226 with only the catches 34 of the plunger locking mechanisms 14a, 14b, 14c extending radially outwardly beyond the arc.

When the plunger locking assembly 100 is compression mounted on the plunger 204, the plunger retention member 16a advantageously prevents or substantially impedes inadvertent or otherwise undesired or unintentional displacement of the plunger locking assembly 100 from its nested position within the compartment 234 of the plunger 204 during use of the syringe 200. Accordingly, displacement of the plunger locking assembly 100 from its nested position within the compartment 234 is typically only enabled by intentionally manually grasping the plunger retention member 16a applying a significant radially outward directed force and/or twisting force thereto that is sufficient to overcome the resistance to outward rotation of the living hinges on the extension segments 60a, 60b of the first and second retention arms 48, 50, for example, when it is desired to substitute the plunger locking assembly 100 for the plunger locking assembly 10.

Figure 21:
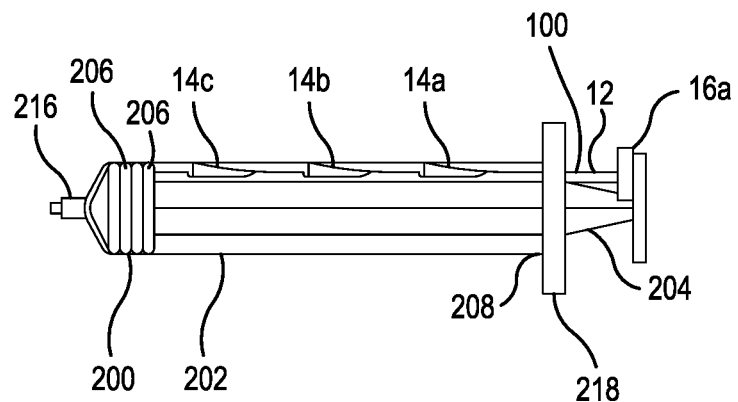
FIG. 21 shows the plunger and plunger locking assembly of FIG. 14 fully depressed into the barrel of FIG. 4 at the outset of a fat harvesting procedure.

While the plunger locking assembly 100 remains compression mounted on the plunger 204, the practitioner inserts the plunger 204 and associated plunger locking assembly 100 completely into the plunger 204 so that the stopper 206 and the inner end 222 of the plunger 204 are adjacent to the closed end 210 of the barrel 202 while the outer end 224 of the plunger 204 and plunger retention member 16a protrude out the open end 208 of the barrel 202 as shown in FIG. 21. The practitioner then couples a specialized fat harvesting or fat re-injection cannula (not shown) with the cannula connector 216 on the closed end 210 of the barrel 202 to provide a fluid-tight (i.e., non-leaking) coupling therebetween and enable fluid communication between the lumen of the cannula and the interior of the barrel 202, thereby rendering the syringe 200 operational for fat harvesting and/or fat re-injection applications.

In order to fully insert the plunger 204 and associated plunger locking assembly 100 into the barrel 202, it is necessary for the practitioner to manually apply the catch depression force to the free end 38 of the catch 34 of each plunger locking mechanisms 14a, 14b, 14c one-by-one as the plunger 204 is manually displaced into the barrel 202. This rotates each catch 34 radially inward about its hinge 36 into its respective travel slot 30, thereby transitioning each catch 34 to its stressed position and sufficiently reducing the catch extension distance to permit each catch 34 to clear the lip of the barrel 202 at the open end 208 thereof during insertion into the barrel 202. Once the catch 34 is inside the barrel 202, the side wall 212 of the barrel 202 maintains each catch 34 depressed within its travel slot 30 so that the catch 34 does not disrupt slidable displacement of the plunger 204 in the barrel 202 while the catch 34 resides therein. As such, the catches 34 of all of the plunger locking mechanisms 14a, 14b, 14c are in their stressed positions when the plunger 204 and associated plunger locking assembly 100 are fully inserted into the barrel 202.

A fat harvesting procedure using the syringe 200 and associated plunger locking assembly 100 is initiated by inserting the tip of the cannula at the closed end 210 of the syringe 200 into the hypodermis beneath the skin of a patient at the fat harvesting site while maintaining the plunger 204 of the syringe 200 fully depressed into the barrel 202. Once the cannula is at its desired position within the hypodermis, the practitioner gradually partially withdraws the plunger 204 from the interior of the barrel 202 by manually gripping the outer end 224 of the plunger 204 and pulling the outer end 224 away from the barrel 202 which forcibly slidably displaces the stopper 206 within the barrel 202 away from the closed end 210 thereof. Forcible slidable displacement of the stopper 206 within the interior of the barrel 202 away from the closed end 210 creates a space 252 between the stopper 206 and the closed end 210 that is termed a harvested fat chamber.

It is self evident that the harvested fat chamber 252 has a variable volume that is a function of the degree of displacement of the stopper 206 within the interior of the barrel 202. In particular, the stopper 206 and plunger 204 act in the manner of a piston that is slidably positioned at one end of the variable-volume harvested fat chamber 252 relative to the closed end 210 of the barrel 202 that is fixably positioned at the opposite end of the harvested fat chamber 252. Accordingly, the harvested fat chamber 252 increases in volume as the degree of displacement of the stopper 206 in the outward direction away from the closed end 210 increases and conversely decreases in volume as the degree of displacement decreases.

Gradual partial withdrawal of the plunger 204 from the interior of the barrel 202 continues until the first plunger locking mechanism 14a termed the outermost plunger locking mechanism exits the interior of the barrel 202 and, more particularly, until the free end 38 of the catch 34 of the outermost plunger locking mechanism 14a exits the interior of the barrel 202. Immediately upon exiting the interior of the barrel 202, the catch 34 of the outermost plunger locking mechanism 14a disengages from the side wall 212 of the barrel 202 and rotates radially outward about its hinge 36 away from its respective travel slot 30 under the elastic force of the hinge 36, which returns the catch 34 to its unstressed position and restores the catch extension distance to its maximum value. As a result, the free end 38 of the catch 34 extends radially outward beyond the lip of the barrel 202 at the open end 208 thereof which prevents the portion of the plunger locking assembly 10 and associated plunger 204 already displaced from the interior of the barrel 202 from re-entering the barrel 202. The plunger 204 assumes a first or initial incremental withdrawal position when the free end 38 of the catch 34 of the outermost plunger locking mechanism 14a abuts and engages the lip of the barrel 202 at the open end 208. The initial incremental withdrawal position of the plunger 204 defines a first or initial incremental volume of the harvested fat chamber 252 shown in FIG. 22. In the case where the volumetric capacity of the barrel 202 is 60 cc, the first or initial incremental volume is approximately 20 cc.

When the plunger 204 first reaches its initial incremental withdrawal position, the harvested fat chamber 252 is in an evacuated state because the tip of the cannula is encapsulated by the hypodermis which prevents air from entering the chamber 252 as the plunger 204 is withdrawn from the barrel 202. There is also typically a time delay upon the plunger 204 first reaching its initial incremental withdrawal position before fat is drawn into the chamber 252 from the hypodermis due to the semi-solid viscous state of the fat in the hypodermis. As a result, the suction of the vacuum in the harvested fat chamber 252 exerts a strong return force on the plunger 204 into the barrel 202 in the direction of its closed end 210. It is apparent that the outermost plunger locking mechanism 14a effectively counters this return force and advantageously prevents the plunger 204 from being drawn back into the interior of the barrel 202. Specifically, the barrel end engagement face 44 on the outermost plunger locking mechanism 14a abuts, engages and presses against the lip at the open end 208 of the barrel 202 and "locks" the plunger 204 in the initial incremental withdrawal position, thereby desirably maintaining the harvested fat chamber 252 at its initial incremental volume even when the chamber 252 is evacuated. In the absence of the plunger locking assembly 100, it would be necessary for the practitioner to manually maintain a continuous counter force on the plunger 204 which becomes quite tiresome for the practitioner. As such, the plunger locking assembly 100 provides valuable assistance to the practitioner during the fat harvesting procedure.

Eventually the pressure differential between the hypodermis and harvested fat chamber 252 draws sufficient fat residing in the hypodermis into the chamber 252 via the lumen of the cannula to substantially fill the initial incremental volume of the chamber 252 with harvested fat. At this point, the practitioner resumes gradual partial withdrawal of the plunger 204 from the interior of the barrel 202 until the second plunger locking mechanism 14b termed the intermediate plunger locking mechanism exits the interior of the barrel 202, the catch 34 of the intermediate plunger locking mechanism 14b returns to its unstressed position, the catch extension distance is restored to its maximum value and the plunger 204 assumes a second or intermediate incremental withdrawal position defining a second or intermediate incremental volume of the harvested fat chamber 252 shown in FIG. 23. In the case where the volumetric capacity of the barrel 202 is 60 cc, the second or intermediate incremental volume is approximately 40 cc.

The same procedure as described above for the initial incremental volume is repeated for the intermediate incremental volume to substantially fill the intermediate incremental volume of the chamber 252 with harvested fat. At this point, the practitioner again resumes gradual partial withdrawal of the plunger 204 from the interior of the barrel 202 until the third plunger locking mechanism 14c termed the innermost plunger locking mechanism exits the interior of the barrel 202, the catch 34 of the final plunger locking mechanism 14c returns to its unstressed position, the catch extension distance is restored to its maximum value and the plunger 204 assumes a third or final incremental withdrawal position defining a third or final incremental volume of the harvested fat chamber 252 shown in FIG. 24. In the case where the volumetric capacity of the barrel 202 is 60 cc, the third or final incremental volume is approximately 60 cc.

It is noted that if the plunger locking assembly 100 was not firmly secured to the outer end 224 of the plunger 204 by means of the plunger retention member 16a as shown in the instant embodiment, the outer end 20 of the main body 12 of the plunger locking assembly 100 could have an unwanted tendency to flop out of its containment in the compartment 234 formed in the main body 220 of the plunger 204 as the plunger 204 is incrementally withdrawn further and further out of the barrel 202. In the absence of the plunger retention member 16a, the uncontained dangling outer end 20 of the main body 12 would be an undesirable distraction to the practitioner during performance of the fat harvesting procedure and could impair the function of the plunger locking assembly 100 and/or syringe 200. Accordingly, the presence of the plunger retention member 16a at the outer end 20 of the main body 12 of the plunger locking assembly 100 and its use in the above-described manner avoids this undesirable scenario.

It is further within the scope of the present invention to substitute either of the above-described alternate embodiments of the plunger retention member 16b, 16c for the plunger retention member 16a in the instant embodiment so that the alternate plunger retention member 16b or 16c is alternatively positioned at the outer end 20 of the main body 12 of the plunger locking assembly 100. The steps for completing the mounting of either alternate plunger retention member 16b, 16c on the plunger 204 so that the alternate plunger retention member 16b or 16c is in abutment with the outer end 224 of the plunger 204 are readily apparent to the ordinary artisan applying the teaching herein.

Once mounting of either alternate plunger retention member 16b, 16c is completed, the first and second lateral faces 26, 28 of the main body engage the opposing lateral faces 230a, 230b of the serially adjacent vanes 226, the inner end 18 of the main body 12 is positioned adjacent to the inner end 222 of the plunger 204 and the arcuate distal face 24 of the main body 12 is essentially flush with the arc drawn between the distal edges 232 of the serially adjacent vanes 226 with only the catches 34 of the plunger locking mechanisms 14a, 14b, 14c extending radially outwardly beyond the arc in the same manner as described above with respect to the plunger retention member 16a. The alternate plunger retention member 16b or 16c likewise advantageously prevents or substantially impedes inadvertent or otherwise undesired or unintentional displacement of the plunger locking assembly 100 from its nested position within the compartment 234 of the plunger 204 during use of the syringe 200.

In any case, the fat harvesting procedure is completed when the fat drawn into the chamber 252 has reached the final incremental volume and the practitioner has removed the cannula from the harvest site. Upon completion of the procedure, at least a portion of the harvested fat residing in the harvested fat chamber 252 of the barrel 202 is suitable for optional conditioning and re-injection.

Figure 25:
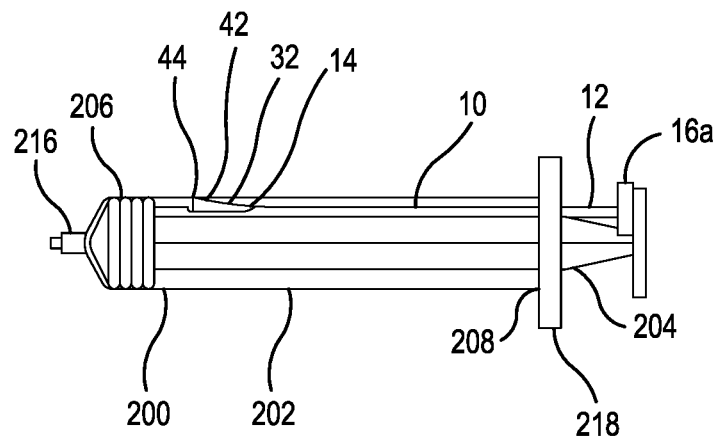
FIG. 25 shows the plunger and the plunger locking assembly of FIG. 20 fully depressed into the barrel of FIG. 4 at the outset of a fat harvesting procedure.
Figure 26:
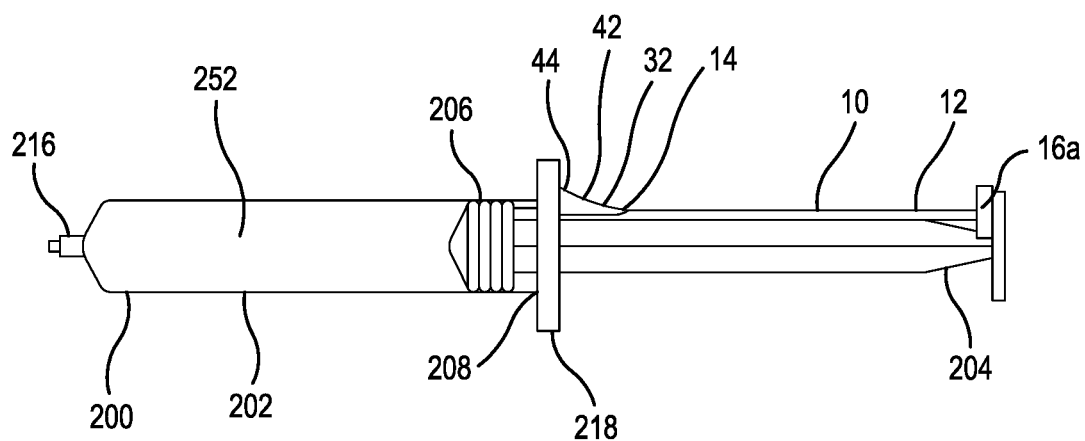
FIG. 26 shows the plunger and the plunger locking assembly of FIG. 20 withdrawn from the barrel of FIG. 4 to a final withdrawal position that defines a final volume of the harvested fat chamber at the completion of the fat harvesting procedure.

A method of use for the plunger locking assembly 10 is essentially the same as described above for the plunger locking assembly 100 except that the plunger locking assembly 10 only has one plunger locking mechanism 14. Therefore, rather than harvesting fat from the hypodermis in incremental steps employing multiple plunger locking mechanisms as in the case of the plunger locking assembly 100, the entire desired volume of fat is harvested from the hypodermis in a single step when using the plunger locking assembly 10. FIGS. 25 and 26 show a method of use for the plunger locking assembly 10. In particular, FIG. 25 shows the plunger 204 of the syringe 200 fully depressed into the barrel 202 and FIG. 26 shows the plunger 204 in a final withdrawal position defining a final volume of the harvested fat chamber 252. Although the drawings do not show specific methods of use for the remaining alternate embodiments of the plunger locking assembly described herein, their methods of use are readily apparent to one of ordinary skill in the art following the teaching of the methods described above.

Figure 22:
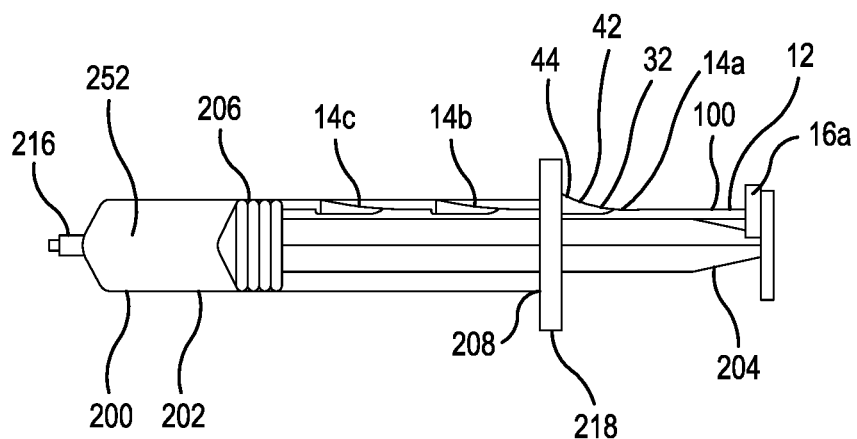
FIG. 22 shows the plunger and plunger locking assembly of FIG. 14 withdrawn from the barrel of FIG. 4 to an initial incremental withdrawal position that defines an initial incremental volume of a harvested fat chamber during the fat harvesting procedure.
Figure 23:
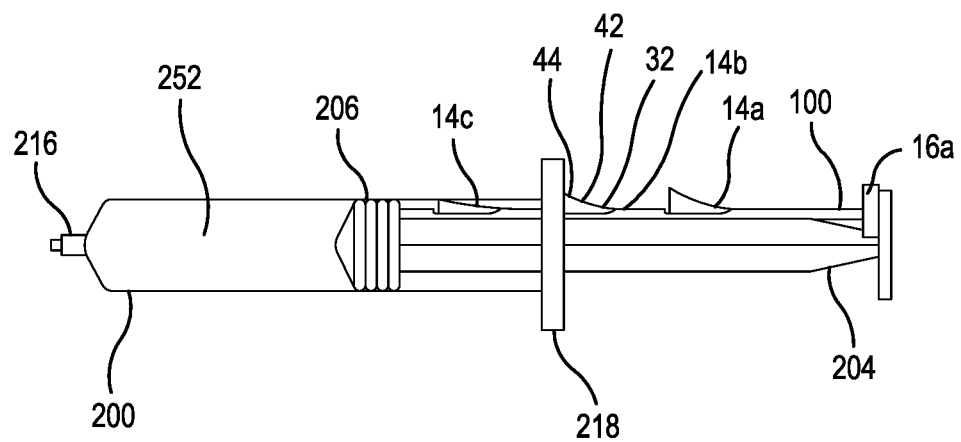
FIG. 23 shows the plunger and plunger locking assembly of FIG. 14 withdrawn from the barrel of FIG. 4 to an intermediate incremental withdrawal position that defines an intermediate incremental volume of the harvested fat chamber during the fat harvesting procedure.
Figure 24:
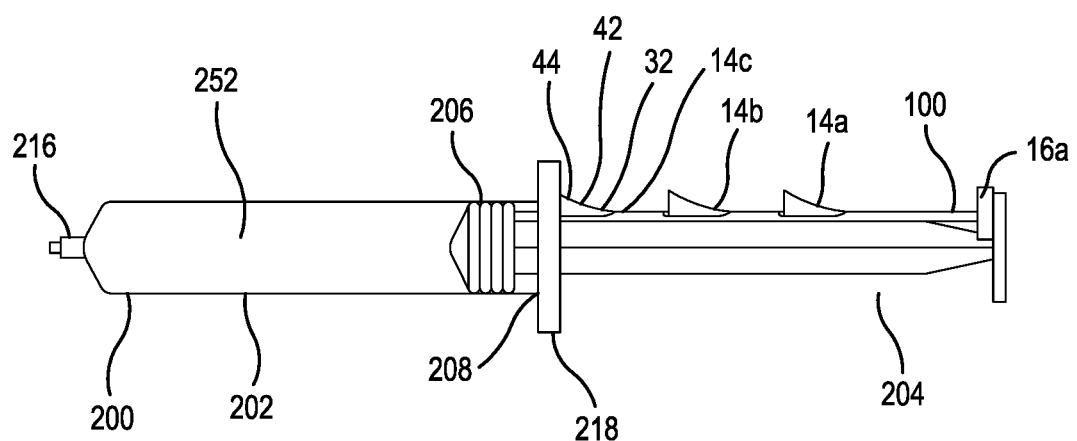
FIG. 24 shows the plunger and plunger locking assembly of FIG. 14 withdrawn from the barrel of FIG. 4 to a final incremental withdrawal position that defines a final incremental volume of the harvested fat chamber at the completion of the fat harvesting procedure.

It is further within the scope of the present invention to employ either embodiment of the plunger locking assembly 10 or 100 in a fat re-injection procedure which is essentially a reverse of the fat harvesting procedure shown in FIGS. 25-26 or FIGS. 21-24, respectively, and described above with reference thereto. Thus, for example, FIG. 24 would show the starting point of a fat re-injection procedure using the plunger locking assembly 100 and syringe 200. The barrel 202 of the syringe 200 is filled to capacity with a fat re-injection material and the plunger 204 is in a withdrawn position, wherein the barrel end engagement face 44 on the innermost plunger locking mechanism 14c abuts, engages and presses against the lip at the open end 208 of the barrel 202 to block the plunger 204 from further displacement into the barrel 202. The practitioner initiates the fat re-injection procedure once the cannula at the closed end 210 of the syringe 200 is at its desired position within the hypodermis at the injection site by manually depressing the barrel interior engagement face 42 on the innermost plunger locking mechanism 14c inward until the barrel end engagement face 44 clears the lip at the open end 208 and no longer engages it. This effectively "unlocks" the plunger 204 and enables the practitioner to displace the plunger 204 into the barrel 202, thereby re-injecting an initial incremental volume of the fat re-injection material into the injection site. However, once the barrel end engagement face 44 of the intermediate plunger locking mechanism 14b engages the lip at the open end 208, the plunger locking assembly 100 "re-locks" the plunger 204 from further displacement into the barrel 202 as shown in FIG. 23.

The same procedure as described above for re-injection of the initial incremental volume of the fat re-injection material into the injection site is then repeated for re-injection of an intermediate incremental volume and a final incremental volume of the fat re-injection material into the injection site as shown in FIGS. 22 and 21, respectively, thereby essentially emptying the barrel 202 and re-injecting substantially all of the fat re-injection material therein into the injection site. The instant fat re-injection procedure employing the plunger locking assembly 100 and syringe 200 enables the practitioner to more carefully control the rate at which the fat re-injection material is re-injected into the body. The instant fat re-injection procedure also enables the practitioner to more easily terminate the entire fat re-injection procedure after only re-injection of the initial incremental volume or after only re-injection of the initial and intermediate incremental volumes of the fat re-injection material into the injection site if desired.

The present plunger locking assembly is broadly characterized as a device that includes structure for locking the position of the syringe plunger in a syringe barrel. The embodiments described herein are exemplary embodiments of such a device. It is understood that alternatives and modifications to these embodiments such as those suggested herein and others that are within the purview of the ordinary artisan, fall within the scope of the present invention. For example, the specific number of plunger locking mechanisms included in the plunger locking assembly is within the purview of one of ordinary skill in the art depending on the particular needs of the specific application for which the plunger locking assembly is employed. As such, the present plunger locking assembly is not limited to any specific number of plunger locking mechanisms. Furthermore, it is readily apparent that each of the plunger retention members 16a, 16b, 16c described herein can be modified within the purview of the ordinary artisan and within the scope of the present invention to adapt the plunger retention member to alternate syringe plunger configurations other than that shown herein as long as the adapted plunger retention member has the structure and ability to retain the plunger locking assembly in a mounted position on the plunger.

We claim:

1. A plunger locking assembly for a syringe having a plunger and a barrel with a hollow barrel interior, wherein the barrel has a barrel longitudinal axis, a closed barrel end, an open barrel end bounded by a peripheral lip and a barrel side wall with a continuously smooth cylindrical barrel inside face longitudinally extending between the closed barrel end and the open barrel end, wherein the barrel inside face laterally bounds the barrel interior and has a barrel concave curvature defining a circular barrel cross section and a barrel inside diameter, wherein the plunger has a plunger longitudinal axis coextensive with the barrel longitudinal axis, a plunger inner end; and a plunger outer end, wherein the plunger inner end is slidably nested within the barrel interior and the plunger outer end is maintained outside the barrel interior at all times, wherein the plunger has a plunger diameter about equal to the barrel inside diameter and a plunger longitudinal surface extending between the plunger inner and outer ends, and wherein the plunger diameter defines a plunger convex arc having a plunger convex curvature corresponding to the barrel concave curvature, thereby enabling slidable nesting of the plunger within the barrel interior, said plunger locking assembly comprising:

a main body having a body inner end, a body outer end, a body distal face and a body proximal face, wherein said main body is adapted to be selectively attachable to and detachable from the plunger and is adapted to releasably nest against the plunger longitudinal surface when said main body is attached to the plunger, wherein said body distal and proximal faces are adapted to be distally and proximally positioned relative to the longitudinal axis of the plunger when said main body is attached to the plunger, wherein said body distal and proximal faces longitudinally extend between said body outer and inner ends, wherein said body distal face has a convex curvature adapted to correspond to the plunger convex curvature such that said body distal face does not extend radially outwardly beyond the plunger convex arc when said main body is attached to the plunger;

a plunger locking mechanism positioned on said main body having a travel slot and a locking member with a hinge and a catch, wherein said catch has an attached end and a free end opposite said attached end, wherein said hinge is positioned at said attached end and rotatably attaches said catch to said main body, wherein said free end has a barrel interior engagement face and a barrel end engagement face, wherein said travel slot is a cut-out extending into said body distal face and said catch is rotatable about said hinge within said travel slot between a stressed position and an unstressed position, wherein said catch is adapted to rotate within said travel slot to said stressed position when said plunger locking mechanism resides within said barrel interior with said barrel interior engagement face in slidable engagement with said barrel inside face and said barrel inside face applies a catch depression force to said barrel interior engagement face such that said catch does not extend radially outward beyond said convex curvature of said body distal face, wherein said catch is adapted to rotate within said travel slot to said unstressed position when said plunger locking mechanism resides outside the barrel interior with said barrel interior engagement face free from engagement with said barrel inside face such that said barrel inside face does not apply said catch depression force to said barrel interior engagement face and said hinge rotationally displaces said barrel end engagement face radially outward beyond said convex curvature of said body distal face into engagement with said peripheral lip of said open barrel end, said peripheral lip thereby blocking said plunger locking mechanism from entering said barrel interior and locking the plunger at a fixed longitudinal lock position within the barrel interior to prevent further slidable displacement of the plunger into the barrel interior; and a plunger retention member fixably attached to said body outer end and adapted to be maintained outside the barrel interior when said catch is in said stressed and unstressed positions and to maintain releasable attachment of said main body to the plunger.

2. The plunger locking assembly of claim 1, wherein said hinge is a living hinge.

3. The plunger locking assembly of claim 1, wherein said hinge is a spring.

4. The plunger locking assembly of claim 1, wherein said catch has a catch extension distance, wherein said catch extension distance is at a maximum value when said catch is in said unstressed position, thereby adapting said barrel end engagement face to engage the peripheral lip, and wherein said catch extension distance is at a reduced value less than said maximum value when said catch is in said stressed position, thereby adapting said barrel end engagement face to clear the peripheral lip and allow further slidable displacement of said plunger locking assembly and the plunger into the barrel interior.

5. The plunger locking assembly of claim 1, wherein said hinge is adapted to automatically elastically return said catch to said unstressed position from said stressed position when said catch depression force is absent.

6. The plunger locking assembly of claim 1, wherein said plunger retention member includes a first retention arm and a second retention arm both adapted to releasably attach to the plunger outer end.

7. The plunger locking assembly of claim 1, wherein said plunger retention member includes a slot adapted to receive and releasably attach to the plunger outer end.

8. The plunger locking assembly of claim 1, wherein said a plunger locking mechanism is a first plunger locking mechanism and said plunger locking assembly has a plurality of plunger locking mechanisms including said first plunger locking mechanism, wherein each of said plurality of plunger locking mechanisms is serially positioned on said main body relative to one another, wherein each of said plurality of plunger locking mechanisms is adapted to lock the plunger at different fixed longitudinal lock positions within the barrel interior to prevent further slidable displacement of the plunger into the barrel interior, and wherein said fixed longitudinal lock position of said first plunger locking mechanism is a first fixed longitudinal lock position.

9. A plunger locking assembly for a syringe having a plunger and a barrel with a hollow barrel interior, wherein the barrel has a barrel longitudinal axis, a closed barrel end, an open barrel end bounded by a peripheral lip and a barrel side wall with a continuously smooth cylindrical barrel inside face longitudinally extending between the closed barrel end and the open barrel end, wherein the barrel inside face laterally bounds the barrel interior and has a barrel concave curvature defining a circular barrel cross section and a barrel inside diameter, wherein the plunger has a plunger longitudinal axis coextensive with the barrel longitudinal axis, a plunger inner end and a plunger outer end, wherein the plunger inner end is slidably nested within the barrel interior and the plunger outer end is maintained outside the barrel interior at all times, wherein the plunger has a plunger diameter about equal to the barrel inside diameter and a plunger longitudinal surface extending between the plunger inner and outer ends, and wherein the plunger diameter defines a plunger convex arc having a plunger convex curvature corresponding to the barrel concave curvature, thereby enabling slidable nesting of the plunger within the barrel interior, said plunger locking assembly comprising:

a main body having a body inner end, a body outer end, a body distal face and a body proximal face, wherein said main body is adapted to be selectively attachable to and detachable from the plunger and is adapted to releasably nest against the plunger longitudinal surface when said main body is attached to the plunger, wherein said body distal and proximal faces are adapted to be distally and proximally positioned relative to the longitudinal axis of the plunger when said main body is attached to the plunger, wherein said body distal and proximal faces longitudinally extend between said body outer and inner ends, wherein said body distal face has a convex curvature adapted to correspond to the plunger convex curvature such that said body distal face does not extend radially outwardly beyond the plunger convex arc when said main body is attached to the plunger; and a plunger locking mechanism positioned on said main body having a travel slot and a locking member with a hinge and a catch, wherein said catch has an attached end and a free end opposite said attached end, wherein said hinge is positioned at said attached end and rotatably attaches said catch to said main body, wherein said free end has a barrel interior engagement face and a barrel end engagement face, wherein said travel slot is a cut-out extending into said body distal face and said catch is rotatable about said hinge within said travel slot between a stressed position and an unstressed position, wherein said catch is adapted to rotate within said travel slot to said stressed position when said plunger locking mechanism resides within said barrel interior with said barrel interior engagement face in slidable engagement with said barrel inside face and said barrel inside face applies a catch depression force to said barrel interior engagement face such that said catch does not extend radially outward beyond said convex curvature of said body distal face, wherein said catch is adapted to rotate within said travel slot to said unstressed position when said plunger locking mechanism resides outside the barrel interior with said barrel interior engagement face free from engagement with said barrel inside face such that said barrel inside face does not apply said catch depression force to said barrel interior engagement face and said hinge rotationally displaces said barrel end engagement face radially outward beyond said convex curvature of said body distal face into engagement with said peripheral lip of said open barrel end, said peripheral lip thereby blocking said plunger locking mechanism from entering said barrel interior and locking the plunger at a fixed longitudinal lock position within the barrel interior to prevent further slidable displacement of the plunger into the barrel interior.

10. The plunger locking assembly of claim 9, wherein said catch has a catch extension distance, wherein said catch extension distance is at a maximum value when said catch is in said unstressed position, thereby adapting said barrel end engagement face to engage the peripheral lip, and wherein said catch extension distance is at a reduced value less than said maximum value when said catch is in said stressed position, thereby adapting said barrel end engagement face to clear the peripheral lip and allow further slidable displacement of said plunger locking assembly and the plunger into the barrel interior.

11. The plunger locking assembly of claim 9, wherein said hinge is adapted to automatically elastically return said catch to said unstressed position from said stressed position when said catch depression force is absent.

12. A plunger locking assembly for a syringe having a plunger and a barrel with a hollow barrel interior, wherein the barrel has a barrel longitudinal axis, a closed barrel end, an open barrel end bounded by a peripheral lip and a barrel side wall with a continuously smooth cylindrical barrel inside face longitudinally extending between the closed barrel end and the open barrel end, wherein the barrel inside face laterally bounds the barrel interior and has a barrel concave curvature defining a circular barrel cross section and a barrel inside diameter, wherein the plunger has a plunger longitudinal axis coextensive with the barrel longitudinal axis, a plunger inner end and a plunger outer end, wherein the plunger inner end is slid ably nested within the barrel interior and the plunger outer end is maintained outside the barrel interior at all times, wherein the plunger has a first vane and a second vane extending radially outward from a line of intersection on the plunger longitudinal axis at a divergence angle from one another with the first vane terminating opposite the line of intersection at a first distal edge and the second vane terminating opposite the line of intersection at a second distal edge, thereby defining a V-shaped longitudinal compartment extending longitudinally along the plunger, wherein the longitudinal compartment is bounded on two sides by a first vane lateral face extending between the first distal edge and the line of intersection and a second vane lateral face extending between the first distal edge and the line of intersection and has an open compartment end extending between the first and second distal edges, wherein the plunger has a plunger diameter about equal to the barrel inside diameter and a plunger convex arc radially extending across the open compartment end and having a plunger convex curvature defined by the plunger diameter, and wherein the plunger convex curvature and barrel concave curvature are correlated to one another to enable slidable nesting of the plunger within the barrel interior, said plunger locking assembly comprising:

a main body having a body inner end, a body outer end, a body distal face, a body proximal face, a first body lateral face and a second body lateral face, wherein said main body is adapted to be selectively attachable to and detachable from the plunger and is adapted to releasably nest within the longitudinal compartment of the plunger with said first body lateral face engaging the first vane lateral face and said second body lateral face engaging the second vane lateral face when said main body is attached to the plunger, wherein said body distal and proximal faces are adapted to be distally and proximally positioned relative to the longitudinal axis of the plunger when said main body is attached to the plunger, wherein said body distal and proximal faces longitudinally extend between said body outer and inner ends, wherein said body distal face has a convex curvature adapted to correspond to the plunger convex curvature such that said body distal face does not extend radially outwardly beyond the plunger convex arc when said main body is attached to the plunger; and a plunger locking mechanism positioned on said main body having a travel slot and a locking member with a hinge and a catch, wherein said catch has an attached end and a free end opposite said attached end, wherein said hinge is positioned at said attached end and rotatably attaches said catch to said main body, wherein said free end has a barrel interior engagement face and a barrel end engagement face, wherein said travel slot is a cut-out extending into said body distal face and said catch is rotatable about said hinge within said travel slot between a stressed position and an unstressed position, wherein said catch is adapted to rotate within said travel slot to said stressed position when said plunger locking mechanism resides within said barrel interior with said barrel interior engagement face in slidable engagement with said barrel inside face and said barrel inside face applies a catch depression force to said barrel interior engagement face such that said catch does not extend radially outward beyond said convex curvature of said body distal face, wherein said catch is adapted to rotate within said travel slot to said unstressed position when said plunger locking mechanism resides outside the barrel interior with said barrel interior engagement face free from engagement with said barrel inside face such that said barrel inside face does not apply said catch depression force to said barrel interior engagement face and said hinge rotationally displaces said barrel end engagement face radially outward beyond said convex curvature of said body distal face into engagement with said peripheral lip of said open barrel end, said peripheral lip thereby blocking said plunger locking mechanism from entering said barrel interior and locking the plunger at a fixed longitudinal lock position within the barrel interior to prevent further slidable displacement of the plunger into the barrel interior.

13. The plunger locking assembly of claim 12, wherein said hinge is a living hinge.

14. The plunger locking assembly of claim 12, wherein said hinge is a spring.

15. The plunger locking assembly of claim 12, wherein said catch has a catch extension distance, wherein said catch extension distance is at a maximum value when said catch is in said unstressed position, thereby adapting said barrel end engagement face to engage the peripheral lip, and wherein said catch extension distance is at a reduced value less than said maximum value when said catch is in said stressed position, thereby adapting said barrel end engagement face to clear the peripheral lip and allow further slidable displacement of said plunger locking assembly and the plunger into the barrel interior.

16. The plunger locking assembly of claim 12, wherein said hinge is adapted to automatically elastically return said catch to said unstressed position from said stressed position when said catch depression force is absent.

17. The plunger locking assembly of claim 12, wherein said a plunger locking mechanism is a first plunger locking mechanism and said plunger locking assembly has a plurality of plunger locking mechanisms including said first plunger locking mechanism, wherein each of said plurality of plunger locking mechanisms is serially positioned on said main body relative to one another, wherein each of said plurality of plunger locking mechanisms is adapted to lock the plunger at different fixed longitudinal lock positions within the barrel interior to prevent further slidable displacement of the plunger into the barrel interior, and wherein said fixed longitudinal lock position of said first plunger locking mechanism is a first fixed longitudinal lock position.

\* \* \* \* \*